United States Patent [19]

Franz et al.

[11] 3,956,417
[45] May 11, 1976

[54] ISOPARAFFIN-OLEFIN ALKYLATION UTILIZING A CONTINUOUS SULFURIC ACID PHASE IN A TUBULAR REACTION ZONE

[75] Inventors: William F. Franz, Cardiner; Edward L. Cole, Fishkill, both of N.Y.

[73] Assignee: Texaco Inc., New York, N.Y.

[22] Filed: Oct. 18, 1974

[21] Appl. No.: 515,943

[52] U.S. Cl. .......................................... 260/683.63
[51] Int. Cl.² ........................................ C07C 3/54
[58] Field of Search .............. 260/683.62, 683.61, 260/683.59, 683.63

[56] References Cited
UNITED STATES PATENTS

| | | | |
|---|---|---|---|
| 2,428,506 | 10/1947 | Van der Valk | 260/683.62 |
| 2,833,840 | 5/1958 | Longwell | 260/683.59 |
| 3,000,994 | 9/1961 | Watson | 260/683.61 |
| 3,175,023 | 3/1965 | Gross et al. | 260/683.59 |
| 3,829,525 | 8/1974 | Cole et al. | 260/683.63 |
| 3,860,531 | 1/1975 | Cole et al. | 260/683.63 |

FOREIGN PATENTS OR APPLICATIONS

792,642   4/1958   United Kingdom ........... 260/683.59

*Primary Examiner*—Delbert E. Gantz
*Assistant Examiner*—G. J. Crasanakis
*Attorney, Agent, or Firm*—T. H. Whaley; C. G. Ries; Douglas H. May, Jr.

[57] ABSTRACT

A process for alkylating isoparaffin hydrocarbons with olefin hydrocarbons for production of high octane gasoline range alkylate wherein the alkylation reaction is performed in the presence of a sulfuric acid alkylation catalyst containing from about 0.0005 to about 0.5 weight percent of a selected micelle forming amphiphilic compound, and wherein the reaction is carried out in a non-backmixed tubular reactor.

12 Claims, 1 Drawing Figure

ISOPARAFFIN-OLEFIN ALKYLATION UTILIZING A CONTINUOUS SULFURIC ACID PHASE IN A TUBULAR REACTION ZONE

BACKGROUND OF THE INVENTION

This invention relates to a process for alkylating an alkylatable isoparaffin hydrocarbon with olefin hydrocarbons. More particularly, this invention relates to a process for producing alkylated hydrocarbon product from $C_4$–$C_6$ isoparaffin hydrocarbons and $C_3$–$C_5$ olefin hydrocarbon reactants utilizing sulfuric acid alkylation catalyst under alkylation reaction conditions including short contact time of hydrocarbon and acid catalyst with substantially no backmixing of the reaction mixture within the reaction zone. This invention further relates to an alkylation process for producing high octane alkylated hydrocarbons having superior quality as components for gasoline motor fuels.

Processes for alkylation of isoparaffin hydrocarbons such as isobutane, isopentane, isohexane and the like with olefin hydrocarbons such as propylene, butylene, amylenes, and the like, are well-known and widely used commercial methods for producing gasoline boiling range hydrocarbons. The $C_5$–$C_{10}$ carbon number range alkylated hydrocarbon products of such alkylation reactions are particularly useful as motor fuel blending stocks because of their high motor octane and research octane values. The selectivity of commercial alkylation processes for highly banched isomers of alkylated hydrocarbons determines the maximum product octane values obtainable. Consequently, process configurations and reaction conditions are being actively sought which favor formation of the highly branched alkylate isomers and which impede side reactions such as olefin polymerization and polymer cracking. The olefin polymers and their cracked products have substantially lower octane values than the preferred alkylate hydrocarbons of similar molecular weight.

Good contact of reactant isoparaffin and olefin hydrocarbons with alkylation catalysts under alkylation reaction conditions is critical to production of desirable high octane alkylate hydrocarbons. In alkylation reactions employing sulfuric acid as catalyst, the olefin reactants are substantially more soluble in the acid catalyst phase than are isoparaffin reactants. Since olefin hydrocarbons undergo polymerization reactions in the presence of the 88–98 percent sulfuric acid solutions commonly employed as alkylation catalysts, operating conditions must be selected to insure good contact of olefin with isoparaffin in the presence of sulfuric acid catalyst so that alkylation reactions will occur in preference to olefin polymerization reactions. In commercial liquid phase alkylation processes this contact of olefin and isoparaffin is obtained by employing isoparaffin in substantial stoichiometric excess to the olefin and subjecting the olefin-isoparaffin-sulfuric acid reaction mixtures to high shear mixing such that emulsions of hydrocarbon and acid are formed. Volume ratios of isoparaffin to olefin charge of from 2/1 to 20/1 are employed to insure the availability of isoparaffin for reaction with the olefin, with isoparaffin to olefin volume ratios of at least 4/1 being preferred.

Generally, it is preferred that the acid phase be maintained as the continuous phase in the reaction emulsions formed such that the hydrocarbon is present as small droplets suspended in the acid phase. Sulfuric acid concentrations of 40 volume percent and above in an alkylation reaction mixture may result in acid-continuous emulsions. Consequently acid concentrations in the range of 40–70 volume percent of an alkylation reaction emulsion are preferred. It has, however, been disclosed that hydrocarbon continuous emulsions of isoparaffin and olefin hydrocarbon with sulfuric acid may be employed as alkylation reaction mixtures, and acid concentrations as low as 10 volume percent in the reaction mixture have been successfully employed.

Reaction temperatures found acceptable in the prior art for sulfuric acid catalyzed alkylation of isoparaffin with olefin are in the range of about −20°F to about 100°F, with reaction temperatures in the range of about 40–60°F being preferred. Such alkylation reactions are exothermic, therefore, the reaction mixture is commonly cooled in the reaction zone to maintain the desired reaction temperatures. Cooling by both direct and indirect heat exchange techniques is commercially practiced. One widely practiced technique is to recover the hydrocarbon phase of a reaction mixture and vaporize a portion of the unreacted isoparaffin under conditions of reduced pressure, thereby substantially reducing the temperature of the unvaporized portion of the hydrocarbon phase. This cold liquid hydrocarbon is then used to cool additional reaction mixture in the reaction zone by indirect heat exchange means.

Alkylation reactions of isoparaffins with olefins have been carried out in both the vapor phase and the liquid phase. In the present application, only those reactions carried out in the liquid phase are under consideration. Therefore, reaction pressures sufficient to maintain reactants in the liquid phase at reaction temperatures are required. Consequently, pressures of from about atmospheric to about 100 psig, or higher are commonly employed in such alkylation reactions. Pressures above those required to maintain reactants in the liquid phase have no noticeable affect upon the alkylation reaction.

Commercial processes for sulfuric acid catalyzed alkylation of isoparaffin with olefins employ back-mixed reactor vessels equipped with high shear mixing devices such as impellers, turbine mixers, etc. Such reaction vessels are sized to provide sufficient residence time for conversion of substantially all olefin within the reaction zone. The high shear mixing is provided to insure good contact of isoparaffin and olefin reactant in the presence of sulfuric acid catalyst. As olefins are substantially more soluble in sulfuric acid catalyst than isoparaffins, and since olefins tend to polymerize in the presence of sulfuric acid catalyst, high shear mixing of the reaction mixture to insure good contact of isoparaffin with olefin is critical to production of a high-octane alkylate product. Consequently, substantial amounts of power are consumed in providing the required good mixing of reactants. This degree of mixing of a back-mixed reactor results in an almost homogeneous reaction mixture, with olefin concentration about equal throughout the reactor volume. As it is desirable to effect essentially complete olefin conversion in the reaction zone for production of higher octane alkylated product, the olefin concentration is quite low throughout the reaction vessel.

Reaction emulsion effluent from such a back-mixed reactor discharges into a settling vessel wherein hydrocarbon phase comprising unreacted isoparaffin and alkylated hydrocarbon is separated from a sulfuric acid catalyst phase by gravity settling. The separated hydrocarbon phase is fractionated, in a fractionation zone, for recovery of an alkylate product fraction and an isoparaffin fraction. Additionally *n*-paraffin impurities of the same or lighter molecular weight as isoparaffin may be fractionated in the fractionation zone. The separated acid phase and isoparaffin fraction are recycled to the alkylation reactor for contact with additional isoparaffin and olefin reactants.

Liquid phase processes for alkylation of isoparaffins with olefins in the presence of acid alkylation catalysts and employing non-back mixed (or tubular) reactors have been proposed. For example, see U.S. Pat. Nos. 3,213,157; 3,169,153; 2,910,522; 3,000,994; and 3,456,033. These processes employ about the same reaction temperatures and pressures, ratios of reactants, residence times, etc. as are employed in commercial back-mixed processes. The advantages of the non-back mixed reactor processes include lower equipment cost and improved alkylate octane value over back-mixed reactor systems. The major disadvantage is the difficulty of maintaining a reaction emulsion of hydrocarbon and acid. Consequently good contact of reactant isoparaffin an olefin hydrocarbons in the presence of acid catalyst is difficult to maintain throughout the length of the non-back mixed reactors. Such non-back mixed reactors may comprise either vertical or horizontal tubular configurations. Generally, isoparaffin and olefin reactants are mixed with acid catalyst at the inlet of a tubular reactor and a reaction mixture comprising unreacted isoparaffin, alkylated hydrocarbon product and acid catalyst is withdrawn from the outlet of the tubular reactor into a settling tank. In the settling tank a hydrocarbon phase comprising isoparaffin and alkylate hydrocarbon is separated by gravity settling from an acid catalyst phase. The hydrocarbon phase from the settling tank is fractionated to recover alkylated hydrocarbon product and isoparaffin. The isoparaffin fraction and acid-catalyst phase is returned to the inlet of the tubular reactor for contact with additional isoparaffin and olefin reactants.

The prior art discloses that such alkylation processes employing non-backed mixed reactors are effective for improving alkylate quality and octane values when acid catalysts are used in which substantial amounts of isoparaffin hydrocarbons may be dissolved. Hydrogen fluoride, which will absorb about 2.7 weight percent isobutane at 80°F, is particularly effective in such alkylation processes. On the other hand alkylation processes employing acid catalysts which do not absorb a substantial amount of isoparaffin reactant do not produce an improvement in alkylate quality and octane number. For example, non-backed mixed processes employing sulfuric acid, which only absorbs about 0.1 percent isobutane at 80°F, are not as efficient and do not produce alkylate of improved quality and octane value, as compared to high-shear, back-mixed alkylation processes.

SUMMARY OF THE INVENTION

Now, according to the method of the present invention, we have discovered an improved process for alkylating an isoparaffin hydrocarbon with an olefin hydrocarbon in the presence of a sulfuric acid alkylation catalyst employing a non-back mixed reactor.

A preferred embodiment of the present invention comprising mixing liquid isoparaffin and olefin hydrocarbon reactants, in an isoparaffin to olefin volume ratio of from 2/1 to about 20/1, with an alkylation catalyst comprising from 98 weight percent to about 88 weight percent sulfuric acid and from about 0.005 to about 0.5 weight percent of a compound for improving absorption of isoparaffin into the acid catalyst, to form a reaction emulsion comprising about 40–60 volume percent acid catalyst and about 60–40 volume percent hydrocarbon reactants; flowing the reaction emulsion through a reaction zone with substantially no back-mixing, at a Reynolds number of at least about 5,000 and a temperature of from about −20°F to about 100°F, for a residence time of from about 5 minutes to about 60 minutes; and centrifugally separating, in a separation zone, reaction effluent from the reaction zone into a hydrocarbon phase, comprising unreacted isoparaffin and alkylated hydrocarbon, and an acid catalyst phase.

Advantages of the present invention include the economic savings of reduced equipment cost and reduced power requirements for a non-back mixed alkylation process as compared to a back-mixed alkylation process employing high shear mixing. Additionally, the process of the present invention produces alkylate of improved quality and octane number. These advantages and others will be described more fully in the detailed description of the invention which follows.

DETAILED DESCRIPTION OF THE INVENTION

Alkylation processes contemplated in the present invention are those wherein isoparaffin hydrocarbons such as isobutane, isopentane, isohexane, etc. are alkylated with olefin hydrocarbons such as propylene, butylenes, pentylenes, etc. Preferably, isobutane is selected as the isoparaffin reactant and olefin reactant is selected from propylene, butylenes, and mixtures thereof. Olefin hydrocarbons in the presence of sulfuric acid alkylation catalysts tend to undergo self polymerization reactions as well as desirable alkylation reactions with isoparaffins hydrocarbons. In order to increase selectivity of olefin conversion to alkylation, a substantial stoichiometric excess of isoparaffin reactant is desirable. Liquid volume ratios of isoparaffin to olefin of from about 2/1 to about 20/1 are contemplated in the present invention and preferably at least 4/1. Reactant hydrocarbon charge streams normally employed in commercial alkylation processes are derived refinery process streams and may contain small amounts of impurities such as *n*-butane, propane, etc. Such impurities are undesirable in large concentration as they occupy alkylation reactor volume, thus decreasing reactor capacity available for the desired reactants. Consequently, process charge streams and/or recycle streams are usually fractionated to remove a substantial portion of such paraffinic impurities.

Alkylation catalysts contemplated for use in the process of the present invention comprise from about 88 weight percent to about 98 weight percent $H_2SO_4$, preferably about 96 weight percent to about 88 weight percent $H_2SO_4$. At $H_2SO_4$ concentrations above about 98 weight percent, the rate of the alkylation reaction decreases and the octane value of alkylate product decreases. At $H_2SO_4$ concentrations below about 88 weight percent, olefin polymerization reactions increase, thus reducing the octane value of the alkylate product. For an effective alkylation catalyst, some water and acid oil must be present with the $H_2SO_4$. That is, fresh $H_2SO_4$ of about 98 weight percent concentration containing about 2 weight percent $H_2O$ has little activity as an alkylation catalyst, and an induction period of contact with hydrocarbon reactant under alkylation reaction conditions is necessary to promote the catalyst activity. During this induction period acid oils, which are high molecular weight reactant products of $H_2SO_4$ and hydrocarbon reactants, are generated. Thus an effective alkylation catalyst will comprise from about 88–98 weight percent $H_2SO_4$, from about 1–8 weight percent $H_2O$ and from about 1–6 weight percent acid oils. In addition, for the process of the invention, a small amount of a compound for increasing solubility of isoparaffin in the sulfuric acid catalysts is required. With such sulfuric acid catalysts comprising $H_2SO_4$, $H_2O$ and acid oils, solubility of isoparaffin in the acid catalyst phase is quite low while olefins are substantially soluble in the catalyst. Consequently, in commercial processes, high shear mixing is employed such that an emulsion of hydrocarbon and acid catalyst is formed to insure contact of isoparaffin and olefin reactants in the presence of the catalyst phase. If such mixing is not provided, then isoparaffin will not effectively contact olefin absorbed in the acid catlyst and the olefin will tend to polymerize rather than alkylate with such isoparaffin. Such olefin polymers from heavy alkylate of $C_9$ and greater carbon number have low octane value. Olefin polymers also crack in the presence of acid catalyst producing light alkylate of $C_5-C_7$ carbon number, which likewise has low octane value. For these reasons, commercial alkylation processes for alkylation of isoparaffins with olefin in the presence of sulfuric acid catalysts have not been successful in nonback mixed reactors without extraneous high shear mixing in the reaction zone to maintain the hydrocarbon-acid catalyst emuslion. However, we have discovered when solubility of isobutane in a sulfuric acid alkylation catalyst is increased to about 1 volume percent or more, high quality alkylate of high octane value can be produced in a nonbacked mixed reactor wherein no extraneous mixing is employed in the tubular reactor zone.

One group of compounds which may be employed advantageously for improving solubility of isoparaffins in sulfuric acid catalyst are amphiphiles which form associations colloids or micelles in acid solution. Amphiphiles are chemical compounds, the molecules of which possess distinct regions of hydrophobic and hydrophilic character. In acid solutions aggregations of the amphiphiles form spherical micelles in which the hydrophobic portion of the amphiphiles are located in the interior of the micelle and the hydrophilic portion of the amphiphiles are at the surface of the micelle. The hydrophilic portion of the micelle is ionic and/or polar whereas the hydrophobic portion is a non-polar hydrocarbon radical preferably comprising a straight chain of 8 to 24 carbon atoms. The hydrocarbon radicals when forming the interior of the micelle are capable of taking into solution the non-polar isoparaffin reactants. Thus, the amphiphiles during the non-polar isoparaffin reactant into solution with the polar sulfuric acid catalyst. The micelles formed are not static species, but rather exist in dynamic equilibrium with the associated polar and non-polar molecules. Consequently, micelles are constantly forming and dissipating, bringing isoparaffin into solution with acid catalyst and releasing it for contact with olefin reactant in intimate contact with the sulfuric acid catalyst.

For use in the present invention, such amphiphilic compounds must form micelles and must be reasonably stable in acid solution. Examples of compounds which are capable of forming micelles and which are known to enhance acid catalyzed alkylation reactions include: N-(alkyl) benzene sulfonamides; N-(alkyl) alkyl sulfonamides, alkyl sulfonium salts, alkyl phosphonium salts, alkyl benzene sulfonic acids, aliphatic amines, NN'N'' tris (alkyl) phosphonic triamides, ammonium salts and salts of alkyl sulfates. It has been found necessary that such amphiphiles contain at least one aliphatic alkyl radical of 8–24 carbon atoms. The total number of carbon atoms may be as high as 60. Amphiphilic compounds which are preferred in the practice of the present invention are N-(alkyl) benzene sulfonamides wherein the (alkyl) radical attached to the nitrogen atom is a straight chain having from about 10 to 20 carbon atoms, and N-(alkyl) alkyl sulfonamides wherein the (alkyl) radical attached to the nitrogen is a straight chain having from about 10 to 20 carbon atoms and the alkyl radical attached to the sulfur atom is a paraffin or cyclo paraffin radical having from 1 to 6 carbon atoms. A particularly preferred amphiphilic compound is N-(octadecyl) benzene sulfonamide. In addition to a capability for forming micelles in acid solution, such amphiphilic compounds in sufficient concentration tend to form emulsions of acid catalyst and hydrocarbon reactants. Should the concentration of such amphiphilic compounds be too great, the emulsions formed are rather stable and separation of acid catalyst from hydrocarbon is hindered. Rapid separation of alkylation reaction emulsion into a hydrocarbon phase and an acid phase is desirable for effective processing of the hydrocarbon, for recovery of the alkylate product, and for recycle of the separated acid phase as catalyst to the alkylation reaction zone. In view of the emulsion forming tendencies of such amphiphilic compounds, the maximum amount of such compounds used must be carefully controlled. Thus, not more than about 0.5 weight percent of a selected amphiphilic compound should be incorporated into a sulfuric acid alkylation catalyst in order to avoid formation of stable hydrocarbonacid emulsions. Preferably, not more than 0.1 weight percent of the selected amphiphilic compound is employed with the sulfuric acid catalyst. The amount of selected amphiphilic compound must be equivalent at least about 0.0005 weight percent of the sulfuric acid catalyst in order to obtain any substantial benefit in an alkylation process.

Temperatures which may be used in alkylation processes of the present invention are in the range from about −20° to about 100°F. Lower temperatures favor alkylation reactions of isoparaffins with olefins over competing olefin polymerization reactions. However, overall reaction rate decreases at lower temperatures. Preferred alkylation temperatures in the range of about 40°–70°F provide good selectivity for alkylation of isoparaffin with olefin at commercially acceptable reaction rate.

Reaction pressures sufficient to maintain all reactants in the liquid phase are required. Reaction pressures from about 10 to about 150 psig are normally used. Higher pressures do not substantially aid the alkylation reaction.

Residence time of reaction emulsion, comprising reactant hydrocarbons, acid catalyst and alkylate hydrocarbon, in the reaction zone is commonly expressed as olefin space velocity. That is, as volumes of olefin per hour per volume of catalyst ($v/v/hr.$). In the present invention, olefin space velocities in the range of from about 0.05 to about 1.0 volumes olefin per hour per volume of catalyst may be employed when the volume ratio of isoparaffin to olefin is in the range of 2/1 to 20/1, and the reaction emulsion comprises about 40–70 volume percent acid catalyst and reaction temperature is at least about 40°F. Olefin space velocity range, substantially all the olefin is converted in the reaction zone. At higher olefin space velocities all the olefin may not react int the reaction zone. At lower space velocities, side reactions such as cracking and isomerization may become significant. Reactants should be maintained in the reaction zone only for a residence time sufficent for conversion of the olefin reactant at the selected reaction conditions. We have also discovered that the hydrocarbon phase comprising unreacted isoparaffin and alkylate product should be separated from the alkylation acid catalyst as soon as possible after the reaction mixture leaves the reaction zone. A preferred embodiment of the present invention incorporates rapid separation of the reaction effluent into hydrocarbon phase and acid phase and withdrawal of the separated phases without prolonged contact such as is presently experienced in acid settler drums employed in prior art processes. That is, we have discovered that limiting contact of hydrocarbon reactants and products with acid catalyst to as nearly as possible the time required for conversion of olefin reactant substantially improves the quality and octane value of the alkylate product.

In the present invention, a non-back mixed, tubular reactor is contemplated. Extraneous high shear mixing of reactants in the reaction zone is not contemplated. We have discovered that by following the method of the present invention isoparaffin hydrocarbons may be alkylated with olefin hydrocarbons in the presence of sulfuric acid alkylation catalyst in a non-back mixed reactor without extraneous, high shear mixing in the reaction zone. This result is unexpected, for heretofore it has been experienced that high shear mixing is required in the reaction zone to maintain good contact of isoparaffin and olefin in the presence of sulfuric acid alkylation catalyst. In the present invention, we have discovered that addition of selected micelle forming amphiphilic compounds, as hereinabove described, to the sulfuric acid alkylation catalyst allows the desired alkylation reaction to proceed in a nonback mixed reactor without the use of extraneous mixing.

In the practice of our invention we use an elongated tubular reactor having an inlet and an outlet end. The reactor diameter is chosen such that the Reynolds number ($N_{RE}$) of the following reaction emulsion is at least about 5,000 $N_{RE}$, and preferably is in the range of about 5,000–20,000 $N_{RE}$. Higher Reynolds numbers do not contribute substantially to the alkylation reaction. At Reynolds numbers below about 5,000 $N_{RE}$, the reaction emulsion may not be maintained and may separate into a hydrocarbon phase and an acid phase. Should separation occur, olefin conversion may be incomplete and/or olefin polymerization reactions may become substantial due to separation of isoparaffin reactant into a separate phase. The length of the tubular reactor is selected to provide the desired olefin space velocity in the range of from about 0.05 to about 1.0 volumes olefin per hour per volume of catalyst. Contact of reactant hydrocarbon with sulfuric acid catalyst for the minimum time required for essentially complete conversion of olefin reactant is preferred.

Reactors in parallel may be employed according to the present invention. By using tubular reactors in parallel, an alkylation process with increased capacity may be operated without the necessity of duplicating process equipment collaterial to the tubular reactors.

Reaction temperatures in the range of about −20°F to about 100°F may be employed in the process of the present invention, as hereinbefore stated. Reactants may be cooled to the desired reaction temperature prior to being introduced into the reaction zone. However, the alkylation reaction is exothermic and cooling must be provided to maintain the desired reaction temperature. External, indirect cooling of the tubular reaction zone is contemplated in the present invention. Particularly effective is the use of a cooling jacket surrounding the tubular reactor. That is, a cold fluid flows in a jacket surrounding the tubular reactor, absorbing the heat of the alkylation reaction. In the case of several tubular reactors in parallel, a reactor configuration of the shell and tube design may be efficiently employed. Flow of the coolant may be co-current or countercurrent to the flow of reactant hydrocarbon. Co-current flow will allow some increase in reaction mixture temperature along the length of the reaction tube, such that the reaction temperature is highest in the portion of the reaction tube wherein the concentration of olefin reactant is lowest. This co-current flow of coolant and reaction mixture, with the concomitant temperature increase along the reactor length, will encourage complete conversion of olefin at low concentrations. With counter current flow of coolant and reaction emulsion, temperatures along the length of the reaction zone can be maintained more nearly equal, if desired.

Coolant may be a refrigerant fluid separately provided for the purpose, or it may comprise a process stream. For an example of the latter, separated hydrocarbon phase comprising unreacted isoparaffin and alkylate product may be flashed at reduced pressure to vaporize a portion of the isoparaffin. The remaining, unflashed hydrocarbon liquid is cooled by vaporization of the isoparaffin, and this cooled liquid may be used as coolant fluid for removing the heat of reaction from the reaction zone.

Efficient transfer of heat from the reaction mixture to the coolant fluid is desirable. Particularly useful aids to the transfer of heat from the reaction emulsion to the wall of the reactor are static mixers of the type marketed by Kenics Corp. (Chemical Engineers Handbook, Fifth Edition, Perry & Chilton, McGraw-Hill Book Co., pp. 19–22). These mixers comprise twisted ribbons of metal of substantially the same width as the diameter of the reactor tube. The twisted ribbons are arranged in a configuration which insures good transverse mixing of the reaction mixture within the reaction zone, thus bringing all the reaction mixture systematically into contact with the cooled tube wall. Heat transfer from a tube equipped with such mixers is many times greater than from a tube so equipped. Other static mixers than these of the "Kenics" design are available although, the Kenics mixer is the simplest of construction and has the lowest pressure drop for an equivalent degree of mixing. In addition to improving heat transfer from the tubular reactor, such static mixers substantially aid maintenance of the reaction emulsion without phase separation in the reaction tube. The uses of such static mixers for improving heat transfer from a tube, and for providing substantial mixing of fluids at a very low pressure drop, are well-known and widely practiced in the prior art.

In the process of the present invention, liquid reaction emulsion effluent exits the tubular reaction zone at the high velocity required to maintain a Reynolds number of at least 5,000 in the reaction zone. The kinetic energy of the flowing reaction effluent is utilized for obtaining rapid separation of the emulsion effluent into a hydrocarbon phase and an acid phase. The separated hydrocarbon phase comprises unreacted isoparaffin and alkylate product, substantially free of acid catalyst. The separated acid phase comprises sulfuric acid alkylation catalyst and a minor amount of hydrocarbon. That is, the separated acid phase comprises about 100–70 volume percent sulfuric acid alkylation catalyst and about 0–30 volume percent hydrocarbon. Additionally, the amphiphilic compound employed with the sulfuric acid alkylation catalyst remains in the separated acid phase.

The kinetic energy of the flowing reaction emulsion is utilized for separation of the hydrocarbon and sulfuric acid alkylation catalyst phases in a mechanical separation device employing the forces of gravity such as a liquid cyclone, centrifuge, etc. Cyclone separators comprise a cylindrical upper section attached to a conical lower section. The inlet stream enters the cylindrical section tangentially, so that a velocity redistribution is involved, resulting in a tangential velocity component which increases with decreasing radius. The flow path invokes a double vortex, with downward spiraling flow at the outside and upward spiraling flow at the center. Spiral velocities may reach values several times the average velocity in the inlet section. The more dense phase of the inlet stream by virtue of its inertia, will tend to move toward the outside wall and pass downward through the conical section, to be removed into a suitable receiver. The less dense phase will pass upward in the central upward spiral flow to be removed at the top of the cyclone through a tube. The centrifugal separating force, or acceleration may range from about 5 times gravity for large, low resistance units to about 2,500 times gravity for small, high pressure drop units. One advantage of such mechanical separation devices, utilizing centrifugal force for separation of the hydrocarbon phase from the acid phase, is effective utilization of the kinetic energy of the reaction zone effluent for separation of the phases is obtained, and additional energy need not be expended. Another advantage is, the hydrocarbon phase may be rapidly separated from the acid phase without the extended period of contact such as experienced in a gravity settling vessel. The overall short contact time of hydrocarbon reactants and alkylate products with sulfuric acid catalyst in the tubular reactor and phase separation device contribute materially to the good quality and high octane value of alkylate product. Undesirable side reactions such as olefin polymerization, cracking, and isomerization which proceed at a slower rate than the alkylation reaction are minimized when contact of hydrocarbon and acid catalyst is limited to essentially the time required for conversion of essentially all the olefin reactant.

A third advantage of a mechanical separation device operating upon the principle of centrifugal separation of the hydrocarbon phase and the acid catalyst phase resides in the characteristic of such devices which allows the degree of separation to be closely controlled and varied within a substantial range. That is, by selection of a properly sized separation device for the expected flow of reaction effluent, the hydrocarbon phase may be recovered substantially free of acid catalyst and the acid phase may be recovered with a controlled hydrocarbon content. For instance, a liquid cyclone is operated such that hydrocarbon phase is withdrawn substantially free of acid, and acid phase is withdrawn at rate to prevent accumulation of acid phase in the cyclone. The rate of acid phase withdrawal may be adjusted to withdraw a volume equivalent only to the volume of acid catalyst entering the cyclone, in which the hydrocarbon content of the acid phase will be quite low, in the range of 0–2 volume percent. Or, if desired, the rate of acid phase withdrawal may be increased to a value somewhat greater than the volume of acid catalyst entering the cyclone in which event the hydrocarbon content of the acid phase will be increased, in the range of 2–30 volume percent. The operation of a sulfuric acid catalyzed alkylation process is substantially improved when acid catalyst phase entering the reaction zone contains a minor portion of hydrocarbon, in the range of 0–30 volume percent and preferably in the range of 3–8 volume percent. The presence of such hydrocarbon in the acid phase improves emulsification of acid phase and hydrocarbon reactants, causing the desired alkylation reactions to predominate over undesired side reactions. By using separation devices operating upon the principle of centrifugal separation of the phases, the hydrocarbon content of the separated acid phase, which is recycled within the alkylation process, may be easily controlled within the desired range.

In operating of such separation devices as described above, we have discovered that separation of acid phase from the hydrocarbon phase can be substantially improved if the reaction emulsion entering the separation device has a hydrocarbon continuous phase with acid catalyst entrained therein. That is, hydrocarbon phase substantially free of acid catalyst is more easily separated from an emulsion wherein the hydrocarbon phase is continuous with small droplets of acid catalyst suspended therein. However, for efficient alkylation of isoparaffin with olefin in a tubular reactor, an emulsion comprising acid catalyst continuous phase is preferred. Acid catalyst continuous phase emulsions with isoparaffin and olefin hydrocarbons which are useful in alkylation reactions may comprise about 40–70 volume percent acid catalyst. We have found that such reaction zone emulsion effluents may readily be converted from acid phase continuous emulsions to hydrocarbon phase continuous emulsions by dilution of the emulsion with additional hydrocarbon to obtain a diluted emulsion comprising 60 volume percent or more hydrocarbon phase. In the process of the present invention, dilution of the reaction zone effluent emulsion is effectively accomplished by circulating a portion of the separated hydrocarbon phase from the outlet of the separation device for contact with reaction zone effluent emulsion at the inlet of said separation device. By this means an acid phase continuous reaction emulsion may be maintained in the reaction zone, and at the reaction zone outlet the emulsion effluent may be converted to an emulsion with a continuous hydrocarbon phase for more efficient separation.

Hydrocarbon phase from the separation device comprises unreacted isoparaffin hydrocarbon and alkylate hydrocarbon product. This separated hydrocarbon phase may be taken directly to a fractionation zone for recovery of isobutane and alkylate hydrocarbon. Preferably, however, the separated hydrocarbon phase is employed to cool the reaction zone to a desired operating temperature. For cooling, the separated hydrocarbon phase from the separation device is passed through a pressure reducing means such that a substantial portion of the isoparaffin hydrocarbon is flash vaporized under conditions approaching adiabatic and the remaining unvaporized hydrocarbon is thereby cooled to a temperature sufficient to cool the reaction zone. The cold hydrocarbon liquid is then preferably passed in indirect heat exchange with the reaction emulsion in the reaction zone. Preferably, the separated hydrocarbon phase is partially vaporized at subatmospheric pressure such that the remaining unvaporized hydrocarbon liquid has a temperature sufficiently low to insure cooling of the reaction emulsion. Conveniently, subatmospheric pressures may be obtained by such means as vacuum pumps, etc. The vaporized hydrocarbon which is substantially all isoparaffin, may be condensed and recycled to the inlet of the reaction zone for contact with additional olefin reactant and acid catalyst. The unvaporized hydrocarbon, after being employed to cool the reaction zone is then passed into a fractionation zone wherein isoparaffin is separated from alkylate product. Isoparaffin from the fractionation zone may be recycled to the inlet of the reaction zone for contact with additional reactant hydrocarbon.

Separated acid phase from the centrifugal separation device is preferably recycled as catalyst to the inlet of the reaction zone for contact with additional olefin and isoparaffin reactants. In a continuous process, as acid strength of the alkylation catalyst declines and as water and acid oil impurities increase, a portion of the recycle acid catalyst may be withdrawn as spent catalyst from the process for removal of such impurities. Fresh sulfuric acid of about 99.5–97% concentration is added to the alkylation process as make-up for the volume of spent catalyst. In this way, sulfuric acid concentration in the acid catalyst may be conveniently controlled within the range of about 98–88 weight percent.

Figure 1:
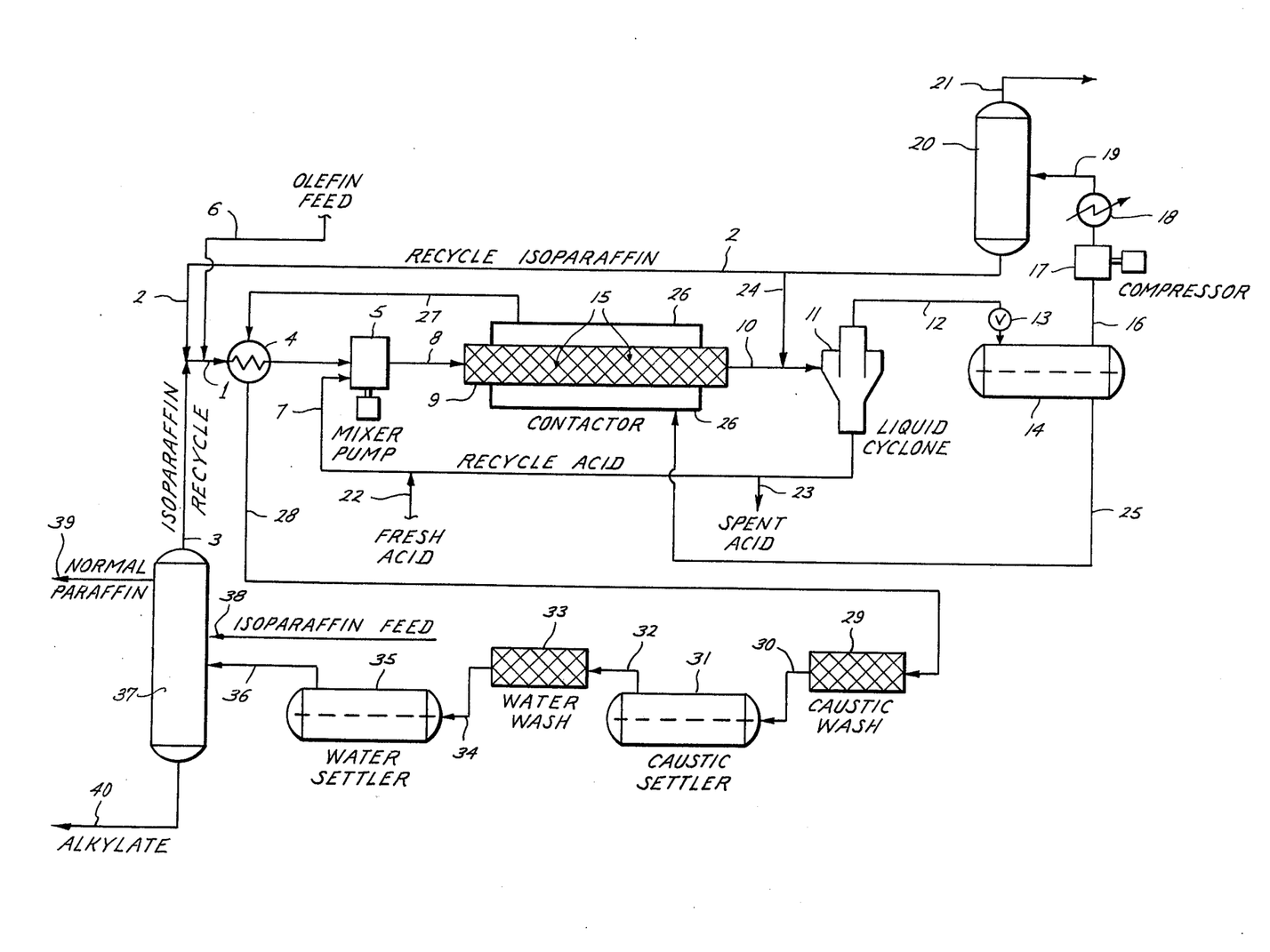
The drawing is a schematic diagram of an alkylation process employing the improvements of the present invention.

In order to better describe the present invention attention is now drawn to the appended drawing. The drawing is a schematic diagram of an alkylation process embodying the improvements of the present invention. Many elements of a unit process, such as valves, pumps, instrumentation, etc. commonly employed but unnecessary for a description of the present invention have been omitted from the drawing for the sake of clarity. Such omitted elements may be readily provided by one skilled in the art. The drawing and the detailed description which follows are not intended to limit the scope of the invention which is described in the appended claims.

In the drawing, isoparaffin in line 1 which is a combined stream isoparaffin from lines 2 and 3, as will hereinafter be described, and olefin hydrocarbon from line 6 are cooled in cooler 4, and pass into mixer 5. Sulfuric acid catalyst from line 7 enters mixer 5. In mixer 5, isoparaffin, olefin, and catalyst are mixed to form an acid continuous phase emulsion comprising about 40–70 volume percent acid catalyst containing about 98–88 weight percent sulfuric acid and from about 0.005 to about 0.5 weight percent of a micelle forming amphiphilic agent and about 60–30 volume percent of hydrocarbon containing isoparaffin and olefin in a volume ratio of from about 2/1 to about 20/1. From mixer 5 the emulsion passes via line 8 into tubular reactor 9 through which the reaction emulsion flows with substantially no back-mixing. In reactor 9 the reaction emulsion flows at a Reynolds number of at least 5,000 for a residence time sufficient to provide an olefin space velocity of from about 0.1 to about 1 volumes olefin per hour per volume alkylation catalyst. Temperature of the reaction emulsion is maintained at a selected temperature of from about −20° to about 100°F and at a pressure from about atmospheric to about 100 psig, or higher, sufficient to maintain all reactants in the liquid phase. Reaction effluent emulsion from reactor 9 passes via line 10 into liquid cyclone 11. Advantageously, additional hydrocarbon may be added to the reaction effluent emulsion before entry into liquid cyclone 11, for converting the reaction effluent emulsion from an acid continuous to a hydrocarbon continuous phase, thus improving separation of acid phase from hydrocarbon phase. Such additional hydrocarbon may be added to the reaction effluent emulsion in line 10 by transferring isoparaffin hydrocarbon from line 2, hereinafter described, via line 24 into line 10. In liquid cyclone 11, the reaction effluent emulsion is separated into a hydrocarbon phase substantially free of acid catalyst and an acid phase containing 0–30 volume percent hydrocarbon.

In the drawing, separated hydrocarbon phase from liquid cyclone 11, comprising unreacted isoparaffin and alkylate hydrocarbon passes through line 12 and pressure reducing valve 13 into flash drum 14. In flash drum 14, a portion of the separated hydrocarbon is flashed at subatmospheric pressure and about adiabatic conditions, thereby cooling the unflashed portion of the hydrocarbon liquid to a temperature below the selected reaction temperature to be maintained in reactor 9. From flash drum 14, vaporized hydrocarbon passes through line 16 and compressor 17 into condenser 18 wherein the hydrocarbon vapor is condensed. From condenser 18, hydrocarbon is charged via line 19 to fractionation column 20 wherein hydrocarbons lower boiling than the isoparaffin hydrocarbon, which may have entered the process as charge stream impurities or may be products of unwanted side reactions, are separated from isoparaffin hydrocarbon. Such lower boiling hydrocarbons are withdrawn from fractionation column 20 via line 21. Isoparaffin hydrocarbon substantially free of such lower boiling hydrocarbons is returned to the process for contact with additional olefin via line 2, as hereinabove described.

In the drawing, acid catalyst phase separated from the hydrocarbon phase in liquid cyclone 11, is recycled via line 7 to mixer 5 for contact with additional isoparaffin and olefin reactants, as hereinabove described. Such recycle acid phase consists of about 70–100 volume percent of acid alkylation catalyst comprising about 98–88 weight percent sulfuric acid, about 1–8 weight percent water, about 1–6 weight percent acid oil, and contains from about 0.0005 to about 0.5 weight percent (based upon sulfuric acid) of a selected micelle forming amphiphilic compound, and about 0–30 volume percent of entrained hydrocarbon. Sulfuric acid concentration in the recycle acid stream is maintained by withdrawing spent acid catalyst, containing water and acid oils, from the process via line 23, and adding, via line 22, fresh sulfuric acid of about 99.5–97 weight percent concentration as make-up for the spent acid removed. Conveniently, the fresh sulfuric acid contains about 0.0005 to 0.5 weight percent of an amphiphilic compound.

In the drawing, cold hydrocarbon liquid from flash drum 14 is passed via line 25 into cooling jacket 26 which surrounds tubular reactor 9. The cold hydrocarbon liquid comprises unreacted isoparaffin hydrocarbon and alkylate hydrocarbon. In cooling jacket 26, the exothermic heat of reaction from the alkylation reaction is transferred through the walls of reactor 9 into the cold hydrocarbon, thus maintaining the temperature of the reactant emulsion within the desired temperature range. After absorbing heat from reactor 9, the hydrocarbon stream flows through cooler 4 for absorption of additional heat from the isoparaffin stream, as hereinabove described. From cooler 4, the hydrocarbon stream passes via line 28 to caustic wash zone 29 wherein any entrained acid is neutralize by reaction with caustic solution. From caustic wash zone 29, the mixture of hydrocarbon and caustic solution passes via line 30 into caustic settler 31 wherein the mixture separates by gravity settling into a hydrocarbon phase and a caustic phase. Hydrocarbon phase from caustic settler 31 passes via line 32 into water wash zone 33 wherein the hydrocarbon phase is contacted with water for removal of any entrained caustic. From water wash zone 33, the hydrocarbon water mixture passes via line 34 to water settler 35 wherein water is separated from the hydrocarbon by gravity settling. From water settler 35, water washed hydrocarbon passes via line 36 into product fractionation column 37.

Isoparaffin feed, to make-up for that consumed in the process, enters product fractionation column 37 via line 38. In column 37 the water washed hydrocarbon and fresh isoparaffin feed are fractionated into an isoparaffin fraction and an alkylate product fraction. The isoparaffin fraction passes from product fractionation column 37 via line 3 into line 1, as hereinabove described for mixture with the isoparaffin stream from line 2. The alkylate product fraction, comprising hydrocarbons of molecular weight greater than the isoparaffin, and having a high octane value is withdrawn from product fractionation column 37 via line 40 for transfer to gasoline blending facilities, not shown. Any normal paraffin hydrocarbons having about the same molecular weight as the isoparaffin hydrocarbon, which are present in either the isoparaffin feed stream or the water washed hydrocarbon stream, may be fractionated in product fractionation column 37 and withdrawn via side drawn line 39.

EXAMPLE I

This example illustrates operation of an alkylation process according to the method of the present invention.

An alkylation hydrocarbon charge mixture, comprising olefin hydrocarbon, fresh isobutane charge and recycle isobutane, and having the composition shown in Table I below, is mixed at a rate of 539 bbl/hr. with recycle catalyst phase comprising about 8.4 volume percent hydrocarbon and about 91.6 volume percent acid catalyst to form a reaction emulsion comprising 60–62 volume percent acid catalyst.

The acid catalyst comprises about 94 weight percent sulfuric acid, about 2 weight percent water, about 4 weight percent acid oil, and contains 0.015 weight percent of the micelle forming amphiphilic compound, N-(octadecyl) benzene sulfonamide.

The reaction emulsion is charged to a tubular reactor cooled by indirect heat exchange with a refrigerant fluid. Said tubular reactor having a diameter of 6 inches and a length of 197 feet. Reaction conditions within the tubular reactor include reactor inlet temperature of 43°F, reactor temperature of 47°F, and reaction emulsion residence time of 30 seconds to provide an olefin space velocity of about 0.06 volumes olefin per hour per volume of acid catalyst. The reaction emulsion is flowed through the tubular reactor at a rate such that the average Reynolds number is 8,350 $N_{RE}$. This Reynolds number is well within the turbulent range, thus the reaction emulsion is maintained throughout the length of the tubular reactor without separation of the phases. Reaction effluent from the tubular reactor outlet is mixed with about 500 bbls. per hour of recycle isobutane for conversion of the emulsion from a hydrocarbon in acid emulsion to an acid in hydrocarbon emulsion. The acid in hydrocarbon emulsion is then passed directly into a liquid cyclone for separation into a hydrocarbon phase and an acid catalyst phase. The acid catalyst phase, having the composition given above, is recycled to the tubular reactor inlet for contact with additional hydrocarbon reactants. About two bbls/hr. of fresh 98 weight percent sulfuric acid containing 0.015 weight percent N-octadecyl benzene sulfonamide is added to the recycle acid stream to maintain the acid concentration therein, and a concomitant amount of acid phase is withdrawn as spent acid.

TABLE I

| HYDROCARBON FEED COMPOSITION | |
|---|---|
| COMPONENT | VOLUME PERCENT |
| $C_3$ | 0.7 |
| $C_3=$ | 0.1 |
| $C_3$ | 4.3 |
| $i-C_4$ | 81.0 |
| $n-C_4$ | 4.0 |
| $i-C_4=$ | 5.0 |
| $n-C_4=$ | 4.3 |
| $i-C_5$ | 0.6 |

The separated hydrocarbon phase is fractionated to yield 100 bbl/hour of a stabilized alkylate product having the properties shown in Table II below.

TABLE II

| ALKYLATE PRODUCT PROPERTIES | |
|---|---|
| GRAVITY | 70.6 |
| COMPOSITION | |
| GC — WEIGHT PERCENT | |
| $C_4-C_5$ | 11.3 |
| $C_6-C_7$ | 7.1 |
| $C_8$ | 72.9 |
| $C_9+$ | 8.7 |
| RON (Clear) | 97.0 |
| MON (Clear) | 93.4 |

EXAMPLE II

This example illustrates operation of a sulfuric acid catalyzed alkylation process employing a tubular reactor, and employing methods of the prior art. Comparison of the results obtained in this example with results of Example I clearly demonstrates the advantages of the improved method of the present invention over the prior art.

The tubular reactor of Example I is used, and operating conditions therein are very close, except a micelle forming amphiphilic compound, such as N-(octadecyl) benzene sulfonamide, is not present in the reaction mixture.

Accordingly, 542 bbl/hour of a hydrocarbon charge, having the composition shown in Table III is mixed with recycle acid catalyst emulsion, comprising about 19 volume percent hydrocarbon and about 81 volume percent acid catalyst, to form a reaction emulsion comprising 60–62 volume percent acid catalyst.

The acid catalyst comprises about 88 weight percent sulfuric acid, 2 weight percent water, and about 10 weight percent acid oil. The acid catalyst is free of amphiphilic compounds which form hydrocarbon micelles in the acid phase.

The reaction emulsion is charged to a tubular reactor cooled by indirect heat exchange with a refrigerant fluid. The tubular reactor has a diameter of six inches and a length of 197 feet. Reaction conditions within the tubular reactor include reactor inlet temperature of 45°F, reactor outlet temperature of 49°F, and reaction emulsion residence time of about 30 seconds to provide an olefin space velocity of about 0.06 volumes olefin per hour per volume of acid catalyst. The flow rate of reaction through the tubular reactor results in a Reynolds number of 8360 $N_{RE}$, which is well within the turbulent flow range.

Reaction effluent from the tubular reactor outlet is separated into a hydrocarbon phase and an acid catalyst phase. The acid catalyst phase is recycled to the tubular reactor inlet for contact with additional hydrocarbon reactants, as hereinabove described. About 2 bbl/hour of fresh 98 weight percent sulfuric acid is added to the recycle acid for maintaining acid concentration, and a concomitant amount of acid phase is withdrawn as spent acid.

TABLE III

| HYDROCARBON FEED COMPOSITION | |
|---|---|
| COMPONENT | VOLUME PERCENT |
| $C_2$ | 0.5 |
| $C_3^=$ | 0.1 |
| $C_3$ | 4.0 |
| $i\text{-}C_4$ | 81.2 |
| $n\text{-}4$ | 4.2 |
| $i\text{-}C_4^=$ | 5.1 |
| $n\text{-}C_4^=$ | 4.3 |
| $i\text{-}C_5$ | 0.4 |
| $n\text{-}C_5$ | 0.2 |

The separated hydrocarbon phase is fractionated to yield 91 bbl/hour of stabilized alkylate hydrocarbon having properties shown in Table IV below.

TABLE IV

| ALKYLATE PRODUCT PROPERTIES | |
|---|---|
| GRAVITY, °API | 68.8 |
| COMPOSITION (GC — WEIGHT PERCENT) | |
| $C_4\text{-}C_5$ | 8.9 |
| $C_6\text{-}C_7$ | 29.3 |
| $C_8$ | 48.2 |
| $C_9+$ | 13.6 |
| RON (Clear) | 87.5 |
| MON (Clear) | 85.0 |

A comparison of the results obtained in Example I, wherein the improvements of the present invention are employed, with results in Example II demonstrates the advantage of the present invention over sulfuric acid catalyzed alkylation processes carried out in tubular reactors employing methods of the prior art. That is, alkylate yield is increased from 91 to 100 bbl/hour at substantially the same reactant charge rate; the alkylate research octane number is increased from 87.5 to 97.0; and the alkylate motor octane number is increased from 85.0 to 93.4. Thus, it is easily seen that by following the method of the present invention substantial improvement in both alkylate yield and alkylate octane number is obtained.

The foregoing descriptions and examples have illustrated an improved sulfuric acid catalyzed process for alkylation of isoparaffin hydrocarbons with olefin hydrocarbons wherein the alkylation reaction is carried out in a non-back mixed reactor, wherein minor amounts of micelle forming amphiphilic compounds are present in the acid catalyst, and wherein reactant and product hydrocarbon are contacted for only a limited time, for production of increased yields of alkylate hydrocarbon having higher octane values as compared to alkylate hydrocarbon produced by prior art methods. It will be apparent to those skilled in the art that variations and modifications of our process included within the scope of the present invention can be similarly employed in the procedures illustrated in the example. Similarly, other isoparaffin and olefin reactants, and other amphiphilic compounds can be employed, and will be apparent to those skilled in the art. Since many variations and embodiments will be apparent to those skilled in the art, the only limitations intended are those contained in the appended claims.

We claim:

1. In a liquid phase alkylation process for alkylating isoparaffin hydrocarbon with olefin hydrocarbon selected from the group consisting of propylene, butylenes, pentylenes, and mixtures thereof in the presence of sulfuric acid alkylation catalyst at alkylation reaction conditions for production of gasoline boiling range alkylate hydrocarbons, wherein said isoparaffin and olefin reactants are mixed with said sulfuric acid alkylation catalyst in a non-backmixed tubular reaction zone forming a reaction emulsion having a continuous acid phase, and wherein the alkylation reaction emulsion is flowed through said non-backmixed tubular reaction zone; the improvement which comprises:

a. maintaining, in said reaction emulsion from about 0.0005 to about 0.5 weight percent, based on sulfuric acid catalyst, of an amphiphilic compound which forms micelles in acid solution, said compound being selected from the group consisting of N-(alkyl) benzene sulfonamides, N-(alkyl) alkyl sulfonamides, alkyl sulfonium salts, alkyl phosphonium salts, alkyl benzene sulfonic acids, aliphatic amines, NN'N'' tris (alkyl) phosphonic triamides, ammonium salts, and salts of alkyl sulfates, the molecules of said compound comprises an ionic hydrophillic region and a hydrophobic region comprising a non-polar aliphatic alkyl radical of 8 to 24 carbon atoms, wherein the amount of said amphiphilic compound is sufficient to dissolve at least about one weight percent of said isoparaffin reactant into said sulfuric acid alkylation catalyst in said reaction emulsion b. flowing said reaction emulsion of step (a) through said non-back mixed tubular reaction zone for a time sufficient to convert essentially all the olefin reactant, at a Reynolds number of at least about 5000 NRE sufficient to maintain the isoparaffin, olefin, and sulfuric acid alkylation catalyst within said reaction emulsion; and c. centrifugally separating, in a separation zone, the reaction zone emulsion effluent from step (b) into a hydrocarbon phase comprising unreacted isoparaffin hydrocarbon and alkylate hydrocarbon, and an acid catalyst phase under dynamic separation conditions such that said separated hydrocarbon phase is immediately removed from contact with said separated acid catalyst phase.

2. The method of claim 1 wherein said isoparaffin reactant and said olefin reactant, in a volume ratio of from about 2/1 to about 20/1 respectively, are mixed with said sulfuric acid alkylation catalyst to form said reaction emulsion having a continuous acid phase, said emulsion comprising from about 40 to about 70 volume percent acid catalyst and from about 60 to about 30 volume percent hydrocarbon; wherein the reaction emulsion is flowed through the reaction zone in the liquid phase without phase separation, at a Reynolds number of from about 5000 $N_{RE}$ to about 10,000 $N_{RE}$ and a temperature of from about −20° to about 100°F; wherein the reaction zone effluent emulsion is separated, by centrifugal separation, into a hydrocarbon phase comprising unreacted isoparaffin and alkylate product, and substantially free of acid catalyst, and into an acid catalyst phase comprising from about 100 to about 70 volume percent of said acid catalyst and from about 0 to about 30 volume percent of said hydrocarbon; wherein said separated acid catalyst phase is recycled for contact with additional isoparaffin and olefin reactants; to said reaction zone and wherein said separated hydrocarbon phase is fractionated for recovery of alkylated hydrocarbon product.

3. The method of claim 2 wherein said action emulsion effluent is diluted with hydrocarbon liquid selected from the group consisting of isoparaffin hydrocarbon reactant and said separated hydrocarbon phase for conversion of said emulsion from a continuous acid phase emulsion to a continuous hydrocarbon phase emulsion, and wherein the acid catalyst in said continuous hydrocarbon phase emulsion is separated in said separation zone of step (c).

4. The method of claim 3 wherein said separated hydrocarbon phase is flashed at subatmospheric pressure to form a vapor phase comprising isoparaffin hydrocarbon and a cold liquid phase comprising isoparaffin hydrocarbon and alkylate hydrocarbon; and wherein exothermic heat of the alkylation reaction is indirectly transferred from said reaction emulsion to said cold liquid phase for maintaining the reaction zone at a selected temperature of from about −20° to about 100°F.

5. The method of claim 4 wherein said vapor phase is fractionated to recover a first isoparaffin hydrocarbon fraction substantially free of any lighter hydrocarbons; and wherein said first isoparaffin stream is recycled for contact with additional isoparaffin and olefin reactants.

6. The method of claim 5, wherein the alkylation reaction zone temperature is in the range of from about 40° to about 60°F.

7. The method of claim 6, wherein said cold liquid phase, after heat exchange with said reaction zone emulsion, is fractionated into a second isoparaffin hydrocarbon fraction and an alkylate hydrocarbon product fraction; and wherein said second isoparaffin hydrocarbon fraction is recycled for contact with additional isoparaffin and olefin reactants.

8. The method of claim 7, wherein the isoparaffin hydrocarbon is selected from the group consisting of isobutane, isopentane, and isohexane and mixtures thereof; and wherein the olefin hydrocarbon is selected from the group consisting of propylene, butylenes, and mixtures thereof.

9. The method of claim 8, wherein said sulfuric acid catalyst comprises from about 98 to about 88 weight percent sulfuric acid, from about 1 to about 8 weight percent water, and from about 1 to about 6 weight percent acid oil.

10. The method of claim 9, wherein the micelle forming amphiphilic compound is selected from N-alkyl (benzene) sulfonamides having a normal alkyl radical of from about 10 to about 20 carbon atoms.

11. The method of claim 9, wherein the micelle forming amphiphilic compound is N-octadecyl (benzene) sulfonamide.

12. The method of claim 9, wherein the micelle forming amphiphilic compound is selected from N-(alkyl) alkyl sulfonamides wherein said (alkyl) radical connected to said nitrogen is normal paraffin having from about 10 to about 20 carbon atoms, and wherein said alkyl radical attached to the sulfur atom is selected from alkyl and cyclo alkyl radicals having 1 to 6 carbon atoms.

* * * * *

UNITED STATES PATENT AND TRADEMARK OFFICE
CERTIFICATE OF CORRECTION

PATENT NO. : 3,956,417
DATED : May 11, 1976
INVENTOR(S) : William F. Franz and Edward L. Cole It is certified that error appears in the above-identified patent and that said Letters Patent are hereby corrected as shown below:

Claim 2, column 17, line 28, "reactants; to said reaction zone" should be --reactants to said reaction zone;--.

Claim 3, column 17, first line, "said action" should be --said reaction--.

Signed and Sealed this

Eleventh Day of March 1980

[SEAL]

Attest:

Attesting Officer

SIDNEY A. DIAMOND

Commissioner of Patents and Trademarks